(12) United States Patent
Szabocsik

(10) Patent No.: US 9,351,990 B2
(45) Date of Patent: May 31, 2016

(54) HYPERTONIC DEXTRAN SOLUTION AND METHODS OF TREATING AND PREVENTING RECURRENT CORNEAL EROSION

(71) Applicant: Theo Holdings, LLC, Cohasset, MA (US)

(72) Inventor: John M. Szabocsik

(73) Assignee: Theo Holdings, LLC, Cohasset, MA (US)

( * ) Notice: Subject to any disclaimer, the term of this patent is extended or adjusted under 35 U.S.C. 154(b) by 0 days.

(21) Appl. No.: 13/969,032

(22) Filed: Aug. 16, 2013

(65) Prior Publication Data

US 2014/0045786 A1   Feb. 13, 2014

Related U.S. Application Data

(62) Division of application No. 13/200,270, filed on Sep. 22, 2011.

(51) Int. Cl.
| | |
|---|---|
| *A61K 31/721* | (2006.01) |
| *A61K 31/728* | (2006.01) |
| *A61K 31/715* | (2006.01) |
| *A61K 9/00* | (2006.01) |
| *A61J 1/06* | (2006.01) |

(52) U.S. Cl.
CPC ............. *A61K 31/715* (2013.01); *A61K 9/0048* (2013.01); *A61K 31/721* (2013.01); *A61K 31/728* (2013.01); *A61J 1/067* (2013.01)

(58) Field of Classification Search
None
See application file for complete search history.

(56) References Cited

U.S. PATENT DOCUMENTS

| | | | |
|---|---|---|---|
| 3,920,810 A * | 11/1975 | Rankin | 424/78.04 |
| 4,271,144 A | 6/1981 | Holly | |
| 4,597,965 A | 7/1986 | Holly | |
| 5,460,834 A | 10/1995 | Bhagat | |
| 6,455,583 B1 | 9/2002 | Pflugfelder et al. | |
| 6,528,048 B1 | 3/2003 | Koike et al. | |
| RE38,628 E * | 10/2004 | Clark et al. | 424/434 |
| 6,991,096 B2 | 1/2006 | Gottlieb et al. | |
| 7,115,653 B2 | 10/2006 | Baxter et al. | |
| 7,189,697 B2 | 3/2007 | Panjwani | |
| 7,204,995 B2 | 4/2007 | El-Sherif et al. | |
| 2004/0033960 A1 | 2/2004 | Doshi et al. | |
| 2006/0079482 A1 | 4/2006 | Lindstrom | |
| 2006/0106104 A1 | 5/2006 | Vehige et al. | |
| 2009/0157037 A1 | 6/2009 | Iyer et al. | |
| 2010/0144766 A1 | 6/2010 | Pines et al. | |

FOREIGN PATENT DOCUMENTS

WO    9631195 A1    10/1996

OTHER PUBLICATIONS

Holly, F. "Lacrophilic oththalmic demulcents" US Ophthal. Rev. (2008) vol. 3, pp. 38-41.*
Charnock, C. "Are multidose over-the-counter artificial tears adequately preserved'?" Cornea (2006) vol. 25, No. 4, pp. 432-437 (abstract only).*
Das, S. et al "Recurrent corneal erosion syndrome" Surv. Ophthalmol. (2008) vol. 53, No. 1, pp. 3-15.*
Stuart Science Equipment Catalogue, pp. 100-101. (undated) http://www.blanc-labo.com/sites/default/files/produit_pdf/a4000en.pdf. Retrieved from the internet Apr. 16, 2015.*
International Searching Authority, International Search Report and Written Opinion, International Application No. PCT/US2012/056273, Nov. 30, 2012.

* cited by examiner

*Primary Examiner* — Leigh C Maier
(74) *Attorney, Agent, or Firm* — Hinshaw & Culbertson LLP

(57) ABSTRACT

An ophthalmic solution is provided. The ophthalmic solution is hypertonic. The ophthalmic solution includes a polysaccharide having an average molecular weight of between about 40,000 grams per mole and about 150,000 grams per mole. A packaged ophthalmic solution for preventing the ophthalmic solution from being exposed to $CO_2$ and other contaminants is also provided. The ophthalmic solution can be used to treat recurrent corneal erosion. The ophthalmic solution can also be used as a prophylactic to prevent recurrent corneal erosion.

13 Claims, 1 Drawing Sheet

HYPERTONIC DEXTRAN SOLUTION AND METHODS OF TREATING AND PREVENTING RECURRENT CORNEAL EROSION

CROSS-REFERENCE TO RELATED APPLICATION

This application is a division of U.S. application Ser. No. 13/200,270, filed on Sep. 22, 2011, pending, the entire disclosure of which is hereby expressly incorporated by reference.

FIELD OF THE INVENTION

The present invention relates to an ophthalmic hypertonic composition including a water-soluble polysaccharide of glucose having an average molecular weight of between about 40,000 and about 150,000 grams per mole. The ophthalmic composition can be used to treat recurrent corneal erosion. The ophthalmic composition can also be used as a prophylactic to prevent recurrent corneal erosion. The present invention also relates to a packaging for the ophthalmic composition.

BACKGROUND OF THE INVENTION

It is important for the cornea to be transparent with an optically smooth surface for the formation of a sharp visual image on the retina. The normal, healthy cornea is transparent, mostly acellular connective tissue consisting of collagen fibers and mucopolysaccharides. This tissue is called the stroma, which is covered by several layers of epithelial cells on the exterior surface, while its interior surface is covered with a single layer of endothelial cells. The macromolecules of the stroma form a loosely connected matrix that contains about 80% by weight of aqueous fluid. This interstitial fluid of the stroma is nearly isotonic. The tissue, however, behaves as if it were somewhat dehydrated, since it tends to imbibe, i.e. absorb, additional fluid when immersed in physiological saline. This occurs because the additional osmolality of its macromolecular matrix causes a net flow of water into the stroma by osmosis, with the epithelium acting as a semipermeable membrane. This tendency of water absorption is measured in terms of the so-called "imbibition pressure," which is about 40-60 torr for the normal cornea. As the degree of hydration of the stroma increases, the imbibition pressure diminishes. Active transport of electrolytes and thus water out of the stroma by its boundary layers of cells keeps the stromal hydration at its normal, i.e. somewhat dehydrated, level in order to maintain its transparency. As the cornea imbibes water, it becomes progressively more cloudy diminishing visual acuity. A highly edematous cornea scatters so much light that it appears to be quite opaque.

Recurrent corneal erosion (RCE) is the recurrence of corneal erosions, either dystrophic or post-traumatic, not precipitated by nor associated with a dry eye condition. RCE can cause the cornea to be edematous. RCE can be a painful and disabling condition of the cornea that causes considerable interference with visual function due to pain, transient decreased vision, and light sensitivity and anxiety, and often results in patients becoming incapacitated and limited in their daily activities. RCE often develops as a result of three different issues: diabetic keratrophy; neurotrophic keratrophy; and following eye surgery such as Lasik surgery.

Symptomatic treatment of RCE with existing hypertonic salt solutions has been ineffective, or even harmful, since the solute of the solution can readily penetrate the stroma achieving hypertonic levels inside the tissue which causes further imbibition of water with the resulting clouding of the cornea which diminishes visual acuity. Additionally, most patients do not respond to treatment with patching or topical lubricants. Some patients may receive temporary relief, but the corneal erosion recurs, resulting in further pain, transient decreased vision, and light sensitivity.

A need therefore exists for an ophthalmic composition that can be used to effectively treat RCE once it has occurred.

A need also exists for an ophthalmic composition that will act as a prophylactic to prevent RCE from occurring, especially for people who are at an increased risk for developing RCE.

A need further exists for packaged ophthalmic solutions that will maintain the stability of ophthalmic compositions for preventing and treating RCE.

BRIEF SUMMARY OF THE INVENTION

The present invention provides ophthalmic solutions, and packaged ophthalmic solutions for preventing and for treating RCE. In addition, methods of treating RCE using ophthalmic solutions, and methods of preventing RCE using ophthalmic solutions are provided.

In one aspect of the invention, an ophthalmic solution for both preventing and for treating RCE is provided. In particular, the ophthalmic solution comprises between about 5% and 25% by weight of a polymer of glucose having an average molecular weight of between about 40,000 grams per mole and about 150,000 grams per mole; between about 0.5% and 2% by weight NaCl; between about 0.5% and 2% by weight hyaluronic acid; and between about 71% and 94% by weight distilled water. The ophthalmic solution has a pH between about 6.5 and 7.5, has an osmotic pressure of between about 320-350 mOsmol/kg solution, and is hypertonic. Typically, for relatively long-term storage (e.g., more than 30 days), it is desired for the solution to contain a buffer and/or from 0 to less than about 360 ppm $CO_2$, more desirably less than about 100 ppm $CO_2$, by weight of the total composition.

In another embodiment, the polymer of glucose is dextran, which may have an average molecular weight of in the range of from about 60,000 to 80,000 grams per mole and preferably about 70,000 grams per mole.

In another embodiment, the ophthalmic solution contains between about 8% and 12% by weight of dextran.

In one aspect of the invention, a packaged ophthalmic solution product is provided. It has been discovered that the addition of contaminants, such as $CO_2$, into the composition, such as from the atmosphere, would change the pH and effectiveness of ophthalmic compositions in accordance with the invention. The packaged ophthalmic solution comprises a plastic ampoule containing an ophthalmic solution. The ophthalmic solution contained within the plastic ampoule comprises between about 5% and 25% by weight of a polymer of glucose having an average molecular weight of between about 40,000 grams per mole and about 150,000 grams per mole; between about 0.5% and 2% by weight NaCl; between about 0.5% and 2% by weight hyaluronic acid; between about 71% and 94% by weight distilled water; and from 0 to less than about 360 ppm $CO_2$, more desirably less than 100 ppm $CO_2$, by weight of the total composition. The ophthalmic solution of the invention is hypertonic. The packaged ophthalmic solution also includes a foil pouch that provides an effective barrier to prevent transport of $CO_2$ therethrough and into the solution. The foil also prevents transport of water from the solution to the atmosphere. The plastic ampoule is contained and sealed within the foil pouch.

In one embodiment, the foil pouch prevents air, including carbon dioxide ($CO_2$) and oxygen ($O_2$) from entering the plastic ampoule. Additionally, the foil pouch prevents liquid from exiting the plastic ampoule to the atmosphere.

In another aspect of the invention, a method of treating recurrent corneal erosion is provided. An ophthalmic solution is topically administered to the eye. The ophthalmic solution comprises between about 5% and 25% by weight of a polymer of glucose having an average molecular weight of between about 40,000 grams per mole and about 150,000 grams per mole; between about 0.5% and 2% by weight NaCl; between about 0.5% and 2% by weight hyaluronic acid; and between about 71% and 94% by weight distilled water. The ophthalmic solution also has a pH between about 6.5 and 7.5, has an osmotic pressure of between about 320-350 mOsmol/kg solution, and is hypertonic. The ophthalmic solution is administered about every 3 to 8 hours for about 2 to 12 weeks.

In one embodiment, the polymer of glucose is dextran, which may have an average molecular weight of in the range of from about 60,000 to 80,000 grams per mole and preferably about 70,000 grams per mole. The ophthalmic solution may also comprise between about 8% and 12% by weight of dextran.

In another embodiment, the ophthalmic solution further comprises a preservative. Specifically, the ophthalmic solution may comprise thimerosal and/or EDTA.

In a further embodiment, the ophthalmic solution is administered about every 3 to 4 hours for about 7 to 10 weeks.

In another aspect of the invention, a method of preventing RCE is provided. An ophthalmic solution is topically administered to the eye. The ophthalmic solution comprises between about 5% and 25% by weight of a polymer of glucose having an average molecular weight of between about 40,000 grams per mole and about 150,000 grams per mole; between about 0.5% and 2% by weight NaCl; between about 0.5% and 2% by weight hyaluronic acid; between about 71% and 94% by weight distilled water; and from 0 to less than about 360 ppm $CO_2$, more desirably less than about 100 ppm $CO_2$, by weight of the total composition. The ophthalmic solution of the invention has a pH between about 6.5 and 7.5, has an osmotic pressure of between about 320-350 mOsmol/kg solution, and is hypertonic. Optionally, a suitable buffer may be included.

In one embodiment, the ophthalmic solution of the invention is obtained from the packaged ophthalmic solution of the invention within about 4 days prior to the administering.

In a specific embodiment, the ophthalmic solution is administered about every 3 to 8 hours for about 7 to 14 days prior to an eye surgery.

In another embodiment, the ophthalmic solution is administered about every 3 to 4 hours for about 10 days prior to an eye surgery.

In a further embodiment, the ophthalmic solution is administered about every 3 to 8 hours for about 7 to 14 days following an eye surgery.

In another embodiment, the ophthalmic solution is administered at least one time per day to prevent recurrent corneal erosion as a result of diabetic keratrophy.

In another embodiment, the ophthalmic solution is administered at least one time per day to prevent recurrent corneal erosion as a result of neurotrophic keratrophy.

In one embodiment, the polymer of glucose is dextran. The dextran may have an average molecular weight in the range of from about 60,000 to about 80,000 grams per mole and preferably about 70,000 grams per mole. The ophthalmic solution may also comprise between about 8% and 12% by weight of the dextran.

DETAILED DESCRIPTION OF THE INVENTION

Figure 1:
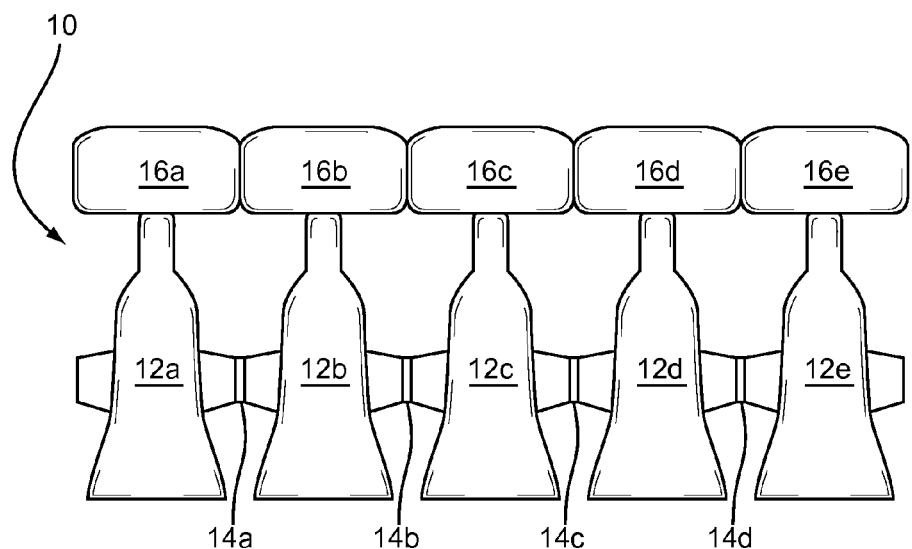
FIG. 1 is an illustration of a packaged ophthalmic product in accordance with the invention.

The ophthalmic composition of this invention can be used to treat RCE. The ophthalmic composition can also be used to prevent RCE from occurring.

A typical colloidal component for use in the ophthalmic solution of the present invention is a polymer of glucose that is chiefly joined through α-1,6-glycosidic linkages, such as dextran, that is obtained by appropriate processing of the high molecular weight product derived from the fermentation of sucrose by the bacteria *Leuconostoc mesenteroides*. Dextran has the molecular formula:

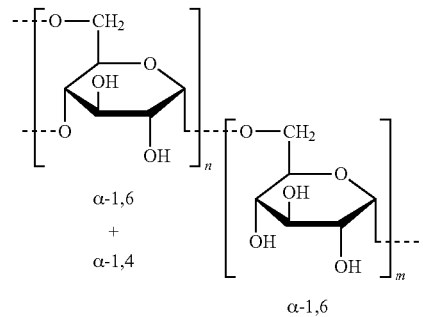

The dextran component of the ophthalmic solution has an average molecular weight of at least about 40,000 and not more than about 150,000 grams per mole, more typically or preferably from about 60,000 to about 80,000 grams per mole and most preferably about 70,000 grams per mole and is obtained by partial hydrolysis and fractionation of the high molecular weight fermentation product. This polysaccharide is highly water-soluble forming aqueous solutions of low viscosity, and carries no net electric charge. The effect of dextran on water surface tension is negligible.

Typically, the ophthalmic solution contains between about 5% and 25% by weight dextran. More typically, the ophthalmic solution contains between about 8% and 12% by weight dextran. Preferably, the ophthalmic solution contains about 10% by weight dextran.

Another hydrophilic polymer useful as the colloidal component of the ophthalmic solution of the present invention is the synthetic polymer polyacrylamide having an average molecular weight between about 20,000 and about 150,000 grams per mole. This polymer is also highly water-soluble forming aqueous solutions of low viscosity, carries no net electric charge, and has a negligible effect on water surface tension.

Aqueous solutions of dextran and polyacrylamide are highly stable and are compatible with the naturally occurring biopolymers found in tears. Both polymers have very low toxicity. Additionally, both polymers are nonionic, and thus the concentration of inorganic salts needed to achieve physiological tonicity has no appreciable deleterious effect on their solubility so that polymer solutions at concentration levels needed to achieve and even surpass the colloidal osmolality of the deturgescent cornea can readily be formulated even in the presence of inorganic electrolytes.

Preferably, the ophthalmic solution is hypertonic. The ophthalmic solution is formulated to provide a colloidal osmotic concentration slightly greater than the corneal swelling pressure.

Additionally, the ophthalmic solution has an osmolality of between about 320 and 350 mOsm/kg. Typically, the ophthalmic solution has an osmolality of between about 325 and 345 mOsm/kg. Most typically, the ophthalmic solution has an osmolality of about 335 mOsm/kg.

The ophthalmic solution may also contain any useful salts, such as, for example, sodium chloride, potassium chloride, calcium chloride, magnesium chloride, and various sulfates, phosphates, borates, nitrates, citrates, acetates, etc.

Typically, the ophthalmic solution contains between about 0.5% and 2% by weight NaCl. More typically, the ophthalmic solution contains between about 0.7% and 1.2% by weight NaCl. Preferably, the ophthalmic solution contains about 0.9% by weight NaCl.

The ophthalmic solution may also contain hyaluronic acid. Hyaluronic acid is an anionic, nonsulfated glycosaminoglycan that is naturally distributed widely throughout connective, epithelial, and neural tissues of the human body. Hyaluronic acid is a polymer of disaccharides, linked via alternating β-1,4 and β-1,3 glycosidic bonds. Hyaluronic acid can be 25,000 disaccharide repeats in length, and has the molecular formula:

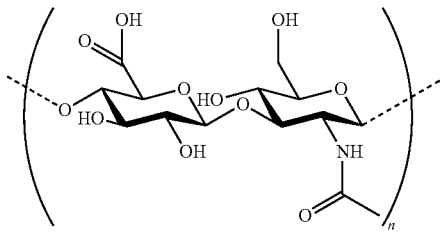

Polymers of hyaluronic acid can range in size from 5,000 to 20,000,000 grams per mole.

Typically, the ophthalmic solution contains between about 0.5% and 2% by weight hyaluronic acid. More typically, the ophthalmic solution contains between about 0.75% and 1.5% by weight hyaluronic acid. Most typically, the ophthalmic solution contains about 1% by weight hyaluronic acid.

Hyaluronic acid increases the lubricity of the ophthalmic solution. The combination of the hyaluronic acid and the dextran in the ophthalmic solution improves the function of the solution in drawing out fluid between the epithelial and basement layers of an eye.

Additionally, the ophthalmic solution may contain a preservative. Preservatives may include, for example, biocides such as benzalkonium chloride, thimerosal, phenylmercuric nitrate, chlorobutanol, methyl paraben, propyl paraben, chlorhexidine digluconate, and sorbic acid and chelating agents, such as for example, di, tri, or tetrasodium ethylene diamine tetraacetate, also known as edetates, may be added at concentrations between about 0.001% and 0.1% by weight. Typically, the ophthalmic composition contains thimerosal and/or ethylenediaminetetraaceticacid (EDTA).

The ophthalmic solution may also contain a buffer or buffering agent to maintain pH, as described herein.

In addition, the ophthalmic solution of the present invention can also contain an eye compatible anesthetic such as, for example, benoxinate, butyl-4-amino-benzoate, naepaine, and phenacaine.

Furthermore, the ophthalmic solution of the present invention may also be used as a carrier for ophthalmic medicants, for example: mydriatics such as tropicamide, atropine, and epinephrine; miotics such as pilocarpine and carbachol; cycloplegics such as cyclopentolate; anti-inflammatories such as dexamethasone and prednisolone; anti-infectives such as sulfas and antibiotics; and vasoconstrictors such as phenylephrine and naphazoline. The medicants may be present in the form of their pharmaceutically acceptable salts or esters.

Another optional ingredient of the ophthalmic solution of the present invention is an eye compatible fluorescing compound of the type used in fluorophotometric determinations such as that used when fitting contact lens. Examples of such fluorescing compounds include sodium fluorescein and fluorexon.

The balance of the ophthalmic solution is distilled water. Typically, the ophthalmic solution contains between about 71% and 94% by weight distilled water. Most typically, the ophthalmic solution contains between about 88% and 90% by weight distilled water.

The ophthalmic solution typically has a pH of between about 6.5 and 7.5. More typically, the ophthalmic solution has a pH of between about 6.8 and 7.2. Most typically, the ophthalmic solution has a pH of about 7.0. A buffer may be included to maintain or help maintain the pH in the foregoing ranges.

The ophthalmic solution has a viscosity of between about 6.5 and 7.5 centistokes. Typically, the ophthalmic solution has a viscosity of between about 6.8 and 7.2 centistokes. Most typically, the ophthalmic solution has a viscosity of about 7.0 centistokes.

Typically, the ophthalmic solution in accordance with the invention contains less than about 360 ppm carbon dioxide, more desirably less than about 100 ppm $CO_2$, all by weight of the total ophthalmic composition.

The ophthalmic solution is formulated to provide a colloidal osmotic concentration slightly greater than the corneal swelling pressure. Topical application of such a solution could diminish or control basal and subepithelial edema that interferes with the adhesion of epithelial cells while providing an effective lubricating layer to the surface of the eye, preventing abrasive sheer forces from the lid margin during blinking.

Figure 2:
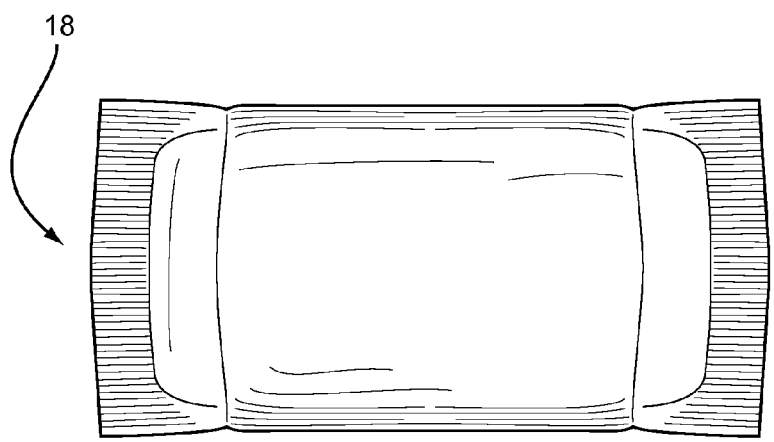
FIG. 2 is an illustration of a foil pouch in accordance with the invention.
Figure 3:
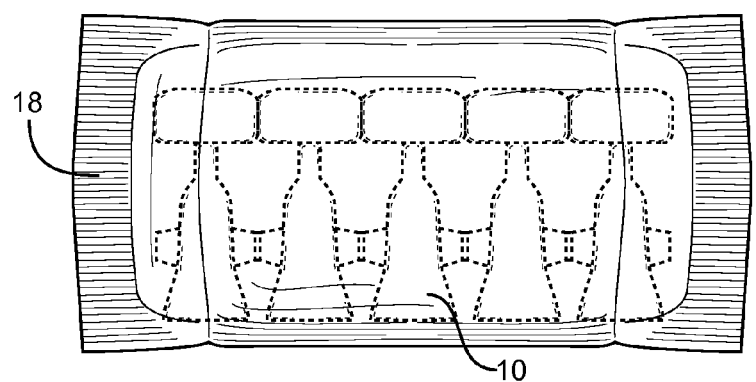
FIG. 3 is a detailed drawing of one embodiment of an ampoule packaged in a foil pouch in accordance with the invention.

A packaged ophthalmic solution 10 in accordance with the invention is generally illustrated in FIGS. 1-3 and is composed of ophthalmic solution 11, plastic ampoules 12a-e which contain the ophthalmic solution 11 and foil pouch 18 which contains ampoules 12a-e. As illustrated in FIG. 1, packaged ophthalmic solution 10 comprises plastic ampoules 12a-e and the ophthalmic solution as described previously contained therein. Any type of plastic that is suitable for storing the ophthalmic solution of the invention may be utilized. Packaged ophthalmic solution 10 is stored within plastic ampoules 12a-e. The plastic ampoules 12a-e as configured include and are connected to each other by side connectors 14a-d. Side connectors 14a-d are designed to allow an individual plastic ampoule 12a-e to be individually disconnected from packaging 10. Each plastic ampoule 12a-e includes a top 16*a-e*. Tops 16*a-e* are designed to be disconnected from plastic ampoules 12*a-e* upon preparation of administration of the ophthalmic solution. Alternatively, it is to be understood that in place of plastic ampoules 12*a-e* could be some other type of individual plastic or other suitable container for the ophthalmic solution of the invention, such as, for example, multiple dose or single dose plastic bottles or pouches or some other plastic container as desired. Such containers, while providing adequate short-term storage and resistance to penetration by $CO_2$, for example, are not suitable for longer term (i.e., more than 30 days or more) resistance to $CO_2$ penetration and consequently would be sealed within a foil container or pouch, such as pouch 18. Foil pouch 18 also prevents transport of water from the solution into the atmosphere.

Plastic ampoules 12*a-e* are each appropriately sized to contain a single dose of the ophthalmic solution. Typically, a single dose of the ophthalmic solution is between about 0.2 and 0.5 mL. More typically, a single dose of the ophthalmic solution is between about 0.25 and 0.4 mL. Most typically, a single dose of the ophthalmic solution is about 0.3 mL.

As illustrated in FIGS. 1-3, packaged ophthalmic solution 10 includes foil pouch 18. Foil pouch 18 can be of any suitable shape and configuration as long as it provides the desired impenetrability to $CO_2$. Foil pouch 18 is crimp sealed to prevent unwanted exposure to gases, such as $CO_2$ or air, which, of course, contains $CO_2$, from passing through and contacting ophthalmic solution 11. The passage of $CO_2$ through plastic ampoules 12*a-e* and into ophthalmic solution 11 would alter the pH of ophthalmic solution 11 contained within plastic ampoules 12*a-e*, resulting in a composition that is too acidic. Foil pouch 18 also prevents liquid (i.e., water) from passing through plastic ampoules 12*a-e* to the atmosphere. The foil should be of a thickness, type and be suitably sealed to prevent passage of any significant amounts (amounts that would be deleterious to the stored solution) of $CO_2$ and/or water through the foil package so as to adequately preserve the stored solution.

The solution in accordance with the invention may also be buffered, in which case absorption of $CO_2$, such as from the atmosphere would not normally be of concern. Suitable buffers include borates, sorbates, phosphates, citrates, carbonates and ascorbates. The amount of buffer will be sufficient under normal circumstances to maintain the pH in a range of from about 6.5 to about 7.5. Suitable amounts of buffering agents may be in the range of 0.05 to 2 mmol (HCl)/L.

Another aspect of the present invention relates to a method of treating RCE. As used herein, the term "treating" refers to: (i) relieving a disease, disorder or condition, i.e., causing regression of the disease, disorder and/or condition; and/or (ii) inhibiting a disease, disorder or condition, i.e., arresting its development.

The method of treating RCE comprises topically administering to an eye an ophthalmic solution as described herein, the ophthalmic solution comprising: between about 5% and 25% by weight of a polymer of glucose having an average molecular weight of between about 40,000 grams per mole and about 150,000 grams per mole; between about 0.5% and 2% by weight NaCl; between about 0.5% and 2% by weight hyaluronic acid; and between about 71% and 94% by weight distilled water. The ophthalmic solution has a pH between about 6.5 and 7.5, has an osmotic pressure of between about 320-350 mOsmol/kg solution, and is hypertonic.

Additionally, the ophthalmic solution may contain a preservative. Preservatives may include, for example, biocides such as benzalkonium chloride, thimerosal, phenylmercuric nitrate, chlorobutanol, methyl paraben, propyl paraben, chlorhexidine digluconate, and sorbic acid and chelating agents, such as for example, di, tri, or tetrasodium ethylene diamine tetraacetate, also known as edetates, may be added at concentrations between about 0.001% and 0.1% by weight. Typically, the ophthalmic solution contains thimerosal and/or ethylene diamine tetraacetic acid (EDTA).

In addition, the ophthalmic solution can also contain an eye compatible anesthetic such as, for example, benoxinate, butyl-4-amino-benzoate, naepaine, and phenacaine.

Furthermore, the ophthalmic solution may also be used as a carrier for ophthalmic medicants, for example: mydriatics such as tropicamide, atropine, and epinephrine; miotics such as pilocarpine and carbachol; cycloplegics such as cyclopentolate; anti-inflammatories such as dexamethasone and prednisolone; anti-infectives such as sulfas and antibiotics; and vasoconstrictors such as phenylephrine and naphazoline. The medicants may be present in the form of their pharmaceutically acceptable salts or esters.

Another optional ingredient of the ophthalmic solution is an eye compatible fluorescing compound of the type used in fluorophotometric determinations such as that used when fitting contact lens. Examples of such fluorescing compounds include sodium fluorescein and fluorexon.

The ophthalmic solution is topically administered about every 3 to 8 hours for about 2 to 16 weeks. Typically, the ophthalmic solution may be administered about every 4 to 6 hours for about 6 to 12 weeks.

The ophthalmic solution may be administered about 3 to 10 times daily for about 2 to 12 weeks. More typically, the ophthalmic solution is administered at least 5 times daily for at least 8 weeks.

Another aspect of the present invention relates to a method of preventing RCE. As used herein, the term "preventing" refers to preventing a disease, disorder or condition from occurring in a subject that may be predisposed to the disease, disorder and/or condition but has not yet been diagnosed as having it.

The method of preventing RCE comprises topically administering to an eye an ophthalmic solution as described herein, the ophthalmic solution comprising: between about 5% and 25% by weight of a polymer of glucose having an average molecular weight of between about 40,000 grams per mole and about 150,000 grams per mole; between about 0.5% and 2% by weight NaCl; between about 0.5% and 2% by weight hyaluronic acid; and between about 71% and 94% by weight distilled water. The ophthalmic solution has a pH between about 6.5 and 7.5, has an osmotic pressure of between about 320-350 mOsmol/kg solution, and is hypertonic.

RCE typically develops as a result of three different issues: diabetic keratrophy; neurotrophic keratrophy; and following eye surgery such as Lasik surgery. The ophthalmic solutions disclosed herein can be topically administered as a prophylactic to prevent RCE from occurring and developing in people who are at risk for developing RCE.

The ophthalmic solution can be administered about every 3 to 8 hours for about 7 to 14 days prior to an eye surgery, such as a Lasik surgery. Typically, the ophthalmic solution is administered about every 3 to 6 hours for about 10 days prior to an eye surgery.

The ophthalmic solution may be administered about 3 to 10 times daily for about 7 to 14 days prior to an eye surgery. More typically, the ophthalmic solution is administered at least 5 times daily for at least 10 days prior to an eye surgery.

The ophthalmic solution can also be administered following an eye surgery to prevent RCE from developing. The ophthalmic solution is topically administered about every 3 to 8 hours for about 7 to 14 days following an eye surgery.

The ophthalmic solution may be administered about 3 to 10 times daily for about 7 to 14 days following an eye surgery. More typically, the ophthalmic solution is administered at least 5 times daily for at least 10 days following an eye surgery.

The ophthalmic solution can be administered to prevent RCE from developing in people who suffer from diabetic keratrophy. The ophthalmic solution is topically administered at least one time per day to prevent RCE as a result of diabetic keratrophy. Typically, the ophthalmic solution is administered at least three times per day. More typically, the ophthalmic solution is administered at least seven times per day.

The ophthalmic solution can be administered to prevent RCE from developing in people who suffer from neurotrophic keratrophy. The ophthalmic solution is topically administered at least one time per day to prevent RCE as a result of neurotrophic keratrophy. Typically, the ophthalmic solution is administered at least three times per day. More typically, the ophthalmic solution is administered at least seven times per day.

EXAMPLES

The present invention is described in more detail with reference to the following non-limiting examples, which are offered to more fully illustrate the invention, but are not to be construed as limiting the scope thereof.

Example 1

An ophthalmic solution with the following formulation can be prepared:

TABLE 1

| Compound | Weight Percent (%) |
| --- | --- |
| Dextran 70 | 10% |
| NaCl | 0.9% |
| Hyaluronic acid | 1% |
| Distilled water | 88.1% |
| $CO_2$ | Less than 360 ppm by weight |

The ophthalmic solution has an osmolality of 350 mOsmol/kg and a pH in the range of 7.0-7.4.

Example 2

The ophthalmic solution of Example 1 can be used topically administered to a patient suffering from RCE. The ophthalmic solution can be topically administered directly on the eye at least 7 times per day for a period of 15 weeks.

Example 3

The ophthalmic solution of Example 1 can be used topically administered to a patient planning to undergo Lasik eye surgery. The ophthalmic solution can be topically administered directly on the eye at least 7 times per day for a period of 10 days prior to the Lasik eye surgery.

While the invention has been described with respect to certain preferred embodiments, as will be appreciated by those skilled in the art, it is to be understood that the invention is capable of numerous changes, modifications and rearrangements, and such changes, modifications and rearrangements are intended to be covered by the following claims.

What is claimed is:

1. A method of treating a human eye for recurrent corneal erosion comprising:
    topically administering to the human eye an ophthalmic solution for treating recurrent corneal erosion, the solution consisting of: between about 5% and 25% by weight of a polymer of glucose having an average molecular weight of between about 40,000 grams per mole and about 150,000 grams per mole; one or more inorganic salts including between about 0.5% and 2% by weight NaCl; between about 0.5% and 2% by weight hyaluronic acid; at least about 71% by weight water; and less than about 360 ppm carbon dioxide;
    wherein the ophthalmic solution has a pH between about 6.5 and 7.5 and has an osmolality of between about 320-350 mOsmol/kg solution;
    wherein the human eye to which the ophthalmic solution is administered suffers from recurrent corneal erosion; and
    wherein the ophthalmic solution is administered to the eye about every 3 to 8 hours for about 2 to 16 weeks.

2. The method of claim 1 further comprising obtaining the ophthalmic solution from a plastic ampoule in a sealed foil pouch; wherein the sealed foil pouch has an interior closed to the external atmosphere and provides a carbon dioxide and oxygen barrier preventing atmospheric carbon dioxide from entering the interior of the sealed foil pouch; wherein the sealed foil pouch is opened within about 30 days prior to the administering.

3. The method of claim 1, wherein the polymer of glucose is dextran and has an average molecular weight of about 70,000 grams per mole.

4. The method of claim 3, wherein the dextran is present in a concentration of between about 8% and 12% by weight of dextran.

5. The method of claim 1, wherein the ophthalmic solution is administered about every 3 to 4 hours for about 7 to 10 weeks.

6. The method of claim 1, wherein the ophthalmic solution is administered at least 5 times daily for at least 8 weeks.

7. The method of claim 1, wherein the ophthalmic solution has less than about 100 ppm carbon dioxide.

8. The method of claim 1, wherein the dose of ophthalmic solution for each administration is between about 0.2 and 0.5 ml.

9. The method of claim 1, wherein the one or more inorganic salts further comprises potassium chloride, calcium chloride, magnesium chloride, a sulfate salt, a phosphate salt, a borate salt, a nitrate salt, a citrate salt, or an acetate salt.

10. The method of claim 1, wherein the water is distilled.

11. The method of claim 1 wherein the hyaluronic acid is present in the solution at a concentration of between about 0.75% and 1.5% by weight.

12. The method of claim 1 wherein the NaCl is present in the solution at a concentration of between about 0.7% and 1.2% by weight.

13. The method of claim 1 wherein the ophthalmic solution has a colloidal osmolality at least equal to the colloidal osmolality of the deturgescent cornea.

* * * * *